US008926569B2

(12) United States Patent
Bisegna et al.

(10) Patent No.: US 8,926,569 B2
(45) Date of Patent: Jan. 6, 2015

(54) PLUNGER COVERS AND PLUNGERS FOR USE IN SYRINGES AND METHODS OF FABRICATING PLUNGER COVERS AND PLUNGERS FOR USE IN SYRINGES

(75) Inventors: Joseph E. Bisegna, Cheswick, PA (US); Jared Neff, Allegheny Township, PA (US)

(73) Assignee: Bayer Medical Care Inc., Indianola, PA (US)

( * ) Notice: Subject to any disclaimer, the term of this patent is extended or adjusted under 35 U.S.C. 154(b) by 690 days.

(21) Appl. No.: 11/686,000

(22) Filed: Mar. 14, 2007

(65) Prior Publication Data

US 2007/0219508 A1    Sep. 20, 2007

Related U.S. Application Data

(60) Provisional application No. 60/782,623, filed on Mar. 15, 2006.

(51) Int. Cl.
*A61M 5/315* (2006.01)
(52) U.S. Cl.
CPC ................................. *A61M 5/31513* (2013.01)
USPC ....................................................... 604/218
(58) Field of Classification Search
CPC ..................... A61M 5/31515; A61M 5/31513; A61M 5/31511; B29C 45/1679
USPC .......................... 604/218, 187, 193, 219, 221
See application file for complete search history.

(56) References Cited

U.S. PATENT DOCUMENTS

| | | | |
|---|---|---|---|
| 4,006,736 A | 2/1977 | Kranys et al. | |
| 4,677,980 A | 7/1987 | Reilly et al. | |
| 5,094,148 A * | 3/1992 | Haber et al. | 92/29 |
| 5,383,858 A | 1/1995 | Reilly et al. | |
| 5,397,313 A * | 3/1995 | Gross | 604/218 |
| 5,782,803 A * | 7/1998 | Jentzen | 604/110 |
| 5,902,276 A * | 5/1999 | Namey, Jr. | 604/218 |
| 6,004,300 A * | 12/1999 | Butcher et al. | 604/222 |
| 6,224,577 B1 | 5/2001 | Dedola et al. | |
| 6,432,089 B1 * | 8/2002 | Kakimi et al. | 604/218 |
| 6,511,459 B1 * | 1/2003 | Fago | 604/181 |
| 6,585,700 B1 * | 7/2003 | Trocki et al. | 604/218 |
| 6,752,789 B2 * | 6/2004 | Duchon et al. | 604/228 |
| 6,817,990 B2 | 11/2004 | Yap et al. | |
| 2004/0006314 A1 * | 1/2004 | Campbell et al. | 604/218 |

FOREIGN PATENT DOCUMENTS

WO        2004035289        4/2004

* cited by examiner

*Primary Examiner* — Aarti B Berdichevsky
*Assistant Examiner* — Bradley Osinski
(74) *Attorney, Agent, or Firm* — David Schram (57) ABSTRACT

A plunger cover for use with a syringe includes a sealing portion adapted to form a seal with the syringe and a central portion adapted to contact fluid within the syringe. The central portion can, for example, be more rigid than the sealing portion. The sealing portion and the central portion are connected in an overmolding process. The sealing portion can, for example, be formed from a thermoplastic elastomer or a thermoplastic polyurethane. The central portion can, for example, be formed from polypropylene, acrylonitrile butadiene styrene, polycarbonate or copolymers thereof.

18 Claims, 10 Drawing Sheets

PLUNGER COVERS AND PLUNGERS FOR USE IN SYRINGES AND METHODS OF FABRICATING PLUNGER COVERS AND PLUNGERS FOR USE IN SYRINGES

CROSS-REFERENCE TO RELATED APPLICATIONS

This application claims priority to U.S. Provisional Application Ser. No. 60/782,623, filed on Mar. 15, 2006, the contents of which are hereby incorporated by reference.

BACKGROUND OF THE INVENTION

The present invention relates generally to plunger covers and to plungers for use in syringes and to methods of fabrication of plunger covers and plungers for use in syringes, and particularly, to plunger covers and to plungers for use in syringes to inject fluids into a patient and to methods of fabrication thereof.

A number of injector-actuated syringes and powered injectors for use in medical procedures such as angiography, computed tomography, ultrasound and magnetic resonance imaging (MRI) have been developed. U.S. Pat. No. 4,006,736, the disclosure of which is incorporated herein by reference, for example, discloses an injector and syringe for injecting fluid into the vascular system of a human being or an animal. Typically, such injectors comprise drive members such as pistons that operatively connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference. Front-loading syringes and syringe plungers for use therewith are also disclosed in U.S. Pat. Nos. 6,585,700 and 6,224,577, the disclosures of which are incorporated herein by reference.

Forward, sliding motion of the syringe plunger within the syringe barrel pressurizes the fluid within the syringe, and the pressurized fluid is injected into that patient via a syringe outlet. A common method of manufacturing syringe plungers adapted, for example, for use in connection with powered injectors is to place an elastomeric, sealing plunger cover over a rigid base. Such rubber covers can, for example, be manufactured by a vulcanization compression molding process. The rubber covers can, for example, be molded into a sheet and then manually hand cut (through a cutting die) from the sheet. Once cut, the rubber covers are, for example, washed in a silicone wash and then assembled onto a plunger base for insertion into a syringe. The process results in substantial material waste and can also result in substantial manufacturing costs and time.

U.S. Pat. No. 5,902,276, the disclosure of which in incorporated herein by reference, discloses a syringe plunger that is formed by a two-shot molding process. A hard plastic core is first formed in a first mold. Subsequently, the distal portion of the hard plastic core is overmolded with a soft rubber plunger cover in a second mold. The second overmolding can occur in the second mold while the core is still cooling to effect molecular bonding of the rubber of the cover with the as-yet uncured plastic of the core.

WO 2004/035289, the disclosure of which is incorporated herein by reference, a copy of which is included herewith and made a part hereof, discloses a method of manufacturing plungers for medical syringes wherein the plunger includes at least two parts. In that regard, the plunger includes a plunger body made of a first plastic and a piston body (in the form of a sealing cover) at the front of the plunger body made of a second plastic. The second plastic (an elastomer) is softer than the first plastic (a generally rigid plastic) of the plunger cover. In forming the plunger, the piston body is first formed by injection molding. Then, the plunger body (or a part thereof) is injected molded against or over the piston body.

Although a number of syringe plungers and methods of fabrication or manufacture of syringe plungers have been developed, it is desirable to develop improved syringe plungers and methods of fabrication of syringe plungers.

SUMMARY OF THE INVENTION

In one aspect, the present invention provides a plunger cover for use with a syringe including a sealing portion adapted to form a seal with the syringe and a central portion adapted to contact fluid within the syringe. The central portion can, for example, be more rigid than the sealing portion. The sealing portion and the central portion are connected in an overmolding process. The sealing portion can, for example, be formed from a thermoplastic elastomer or a thermoplastic polyurethane. The central portion can, for example, be formed from polypropylene, acrylonitrile butadiene styrene, polycarbonate or copolymers thereof.

In several embodiments, the sealing portion is injection molded first and the central portion is injection overmolded thereon. In other embodiments, the central portion is injection molded first and the sealing portion is injection overmolded thereon. In several preferred embodiments, the sealing portion is injection molded first and the central portion is injection overmolded thereon. The material for the sealing portion and the material for the central portion can be selected so that molecular bonding occurs between the sealing portion and the central portion.

In another aspect, the present provides a plunger for use with a syringe including a plunger cover including a sealing portion adapted to form a seal with the syringe and a central portion adapted to contact fluid within the syringe as described above. The central portion can, for example, be more rigid than the sealing portion. The sealing portion and the central portion are connected in an overmolding process. The plunger further includes a support attached to the plunger cover.

The sealing portion can, for example, includes a radially inward projecting flange that is seated within a seating formed on the support to connect the plunger cover to the support. The support can, for example, include a forward surface adapted to abut the plunger cover to prevent rearward motion of the central portion relative to the support.

In another aspect, the present invention provides a syringe including a syringe body and a plunger slidably positioned within the syringe body. As described above, the plunger includes a plunger cover including a sealing portion adapted to form a seal with the syringe and a central portion adapted to contact fluid within the syringe. The central portion can, for example, be more rigid than the sealing portion. The sealing portion and the central portion are connected in an overmolding process. The plunger further includes a support attached to the plunger cover.

In a further aspect, the present invention provides a method of fabricating a plunger cover for use in a syringe, including: connecting a sealing portion adapted to form a seal with the syringe and a central portion adapted to contact fluid within the syringe in an overmolding process, the central portion being more rigid than the sealing portion. The sealing portion can, for example, be injection molded first and the central portion is injection overmolded thereon. Alternatively, the central portion can be injection molded first and the sealing portion is injection overmolded thereon.

In another aspect, the present invention provides a plunger cover for use with a syringe including a sealing portion adapted to form a seal with the syringe and a central portion adapted to contact fluid within the syringe. The central portion has at least one physiochemical property that differs from the sealing portion. The sealing portion and the central portion are connected in an overmolding process.

In another aspect, the present invention provides a plunger cover for use with a syringe including a sealing portion adapted to form a seal with the syringe and a central portion. The central portion is more rigid than the sealing portion. The sealing portion and the central portion being connected in an overmolding process. In one embodiment, the central portion is positioned forward of at least a portion of the sealing portion and is adapted to contact fluid within the syringe. In another embodiment, the central portion is positioned rearward of a generally central section of the sealing portion and does not contact fluid within the syringe. The central portion can, for example, be overmolded upon the sealing portion. Alternatively, the central portion can be injection molded first and the sealing portion is injection overmolded thereon.

In still a further aspect, the present invention provides a plunger for use with a syringe including a sealing portion adapted to form a seal with the syringe and a central portion adapted to contact fluid within the syringe. The central portion is, for example, more rigid than the sealing portion. The sealing portion and the central portion are connected in an overmolding process. The sealing portion can, for example, be adapted to form an operative connection with a drive member.

The present invention, along with the attributes and attendant advantages thereof, will best be appreciated and understood in view of the following detailed description taken in conjunction with the accompanying drawings.

DETAILED DESCRIPTION OF THE INVENTION

One embodiment of a plunger 10 of the present invention is illustrated in FIG. 1A through 1F. As illustrated, for example, in FIGS. 1D and 1E, plunger 10 includes a plunger cover 20 that contacts the fluid within a syringe 100 (see FIG. 1F) and forms a seal with the inner wall of the generally cylindrical barrel of syringe 100. Syringe 100 is adapted to be removably connected to an injector 200 via, for example, a retaining flange 110 on syringe 100 the cooperates with a retainer on a syringe interface 210 of injector 200. Injector 200 includes a drive member or piston 220 moveable in a reciprocal manner to pressurize fluid within syringe 100.

Plunger cover 20 includes a sealing section 30 formed, for example, from an elastomeric material suitable to form a sealing engagement with the inner wall of syringe 100. Plunger cover 20 further includes a generally central portion 40 formed from a generally rigid polymeric material. In the embodiment of FIG. 1A through 1G, central portion 40 has a conical shape adapted to contact the injection fluid and to mate generally with a conical transition region 120 of syringe 100. Plunger 10 further includes a base, support or support ring 50 to which plunger cover 20 is attached. In that regard, elastomeric sealing portion 30 includes a radially inward projecting flange 32 that is seatable within a seating 52 formed in base 50. Base 50 further includes a forward surface 54 that is shaped to contact and mate generally with a rearward surface of plunger cover 20 and to provide support for plunger cover 20. In that regard, abutment of forward surface 54 with plunger cover 20 limits or prevents rearward motion of plunger cover 20 relative to base or support 50. To limit such rearward motion, forward surface 54 preferably contacts a portion of plunger cover 20 so that at least a portion of rigid central conical portion is in alignment with at least a portion forward surface 54. A rearward surface 56 of base 50 is adapted to be contacted by piston 220.

Preferably, plunger cover 20 is formed in an overmolding process such as disclosed in WO 2004/035289. In an injection overmolding process, an injection molding machine is used which includes a heated screw and barrel that melt polymer to a liquid state. In general, an injection molding machine pushes/injects the molten polymer through a heated manifold system into a mold. Once the polymer is inside the mold, it is cooled to a final shape (as determined by the internal dimensions of the mold), and then ejected. In general, waste material associated with injection molding overmolding processes is less than associated with many other manufacturing processes for multi-component articles. Moreover, the overmolding process can be operated automatically. Once the part is formed and cooled, no additional operations are required.

Figure 1A:
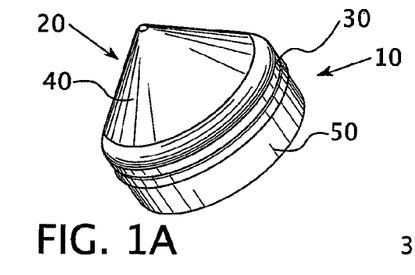
FIG. 1A illustrates a perspective view of an embodiment of a plunger of the present invention.
Figure 1B:
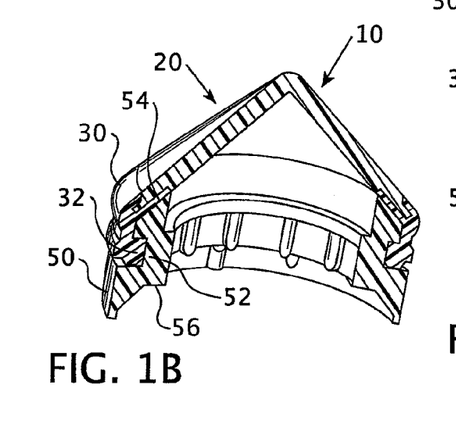
FIG. 1B illustrates a perspective cutaway view of the plunger of FIG. 1A.
Figure 1C:
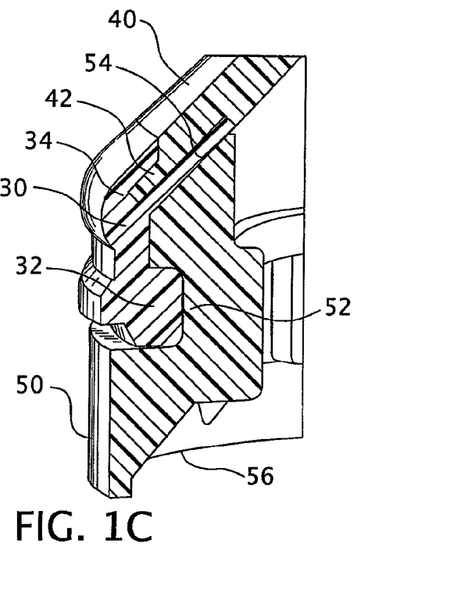
FIG. 1C illustrates an enlarged cutaway view of a portion of the plunger of FIG. 1A.
Figure 1D:
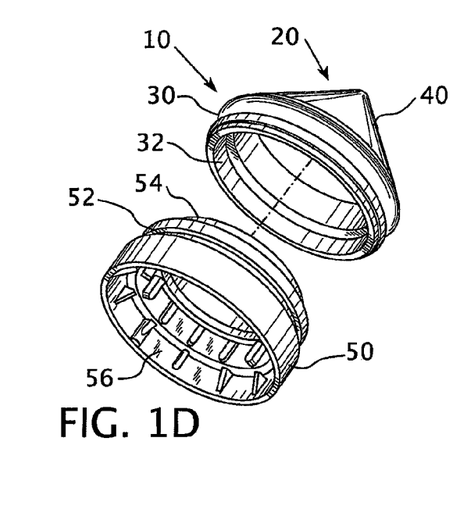
FIG. 1D illustrates a rear perspective, exploded view of the plunger of FIG. 1A wherein the plunger cover is disconnected from the base.
Figure 1E:
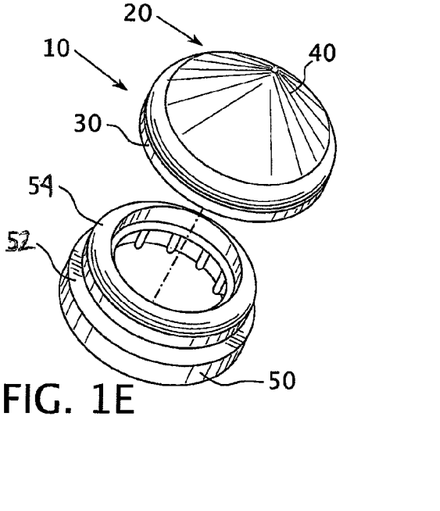
FIG. 1E illustrates a front perspective, exploded view of the plunger of FIG. 1A wherein the plunger cover is disconnected from the base.
Figure 1F:
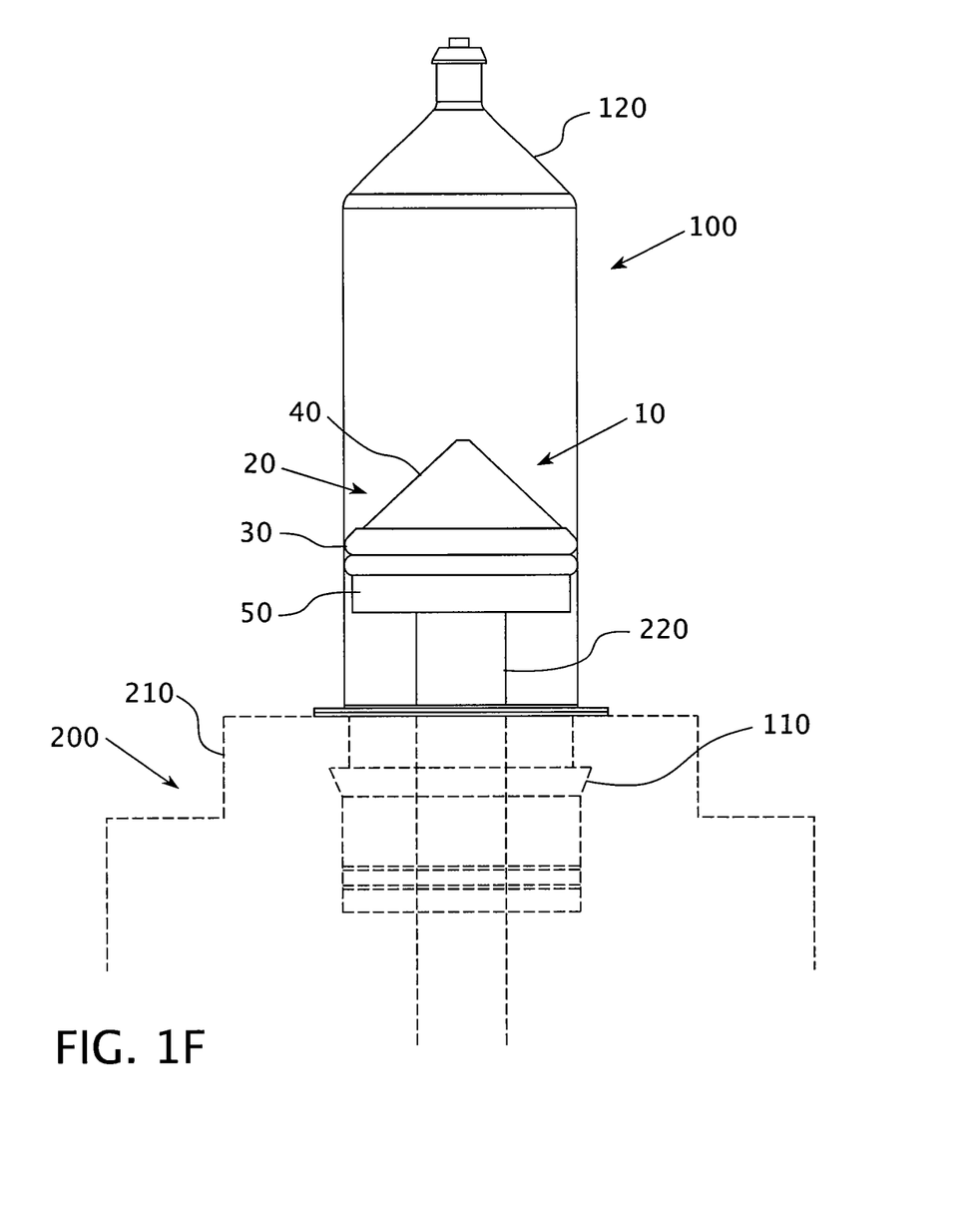
FIG. 1F illustrates a side schematic view of the plunger of FIG. 1A slidably positioned within a syringe that is removably attached to a powered injector.
Figures 2A, 2B:
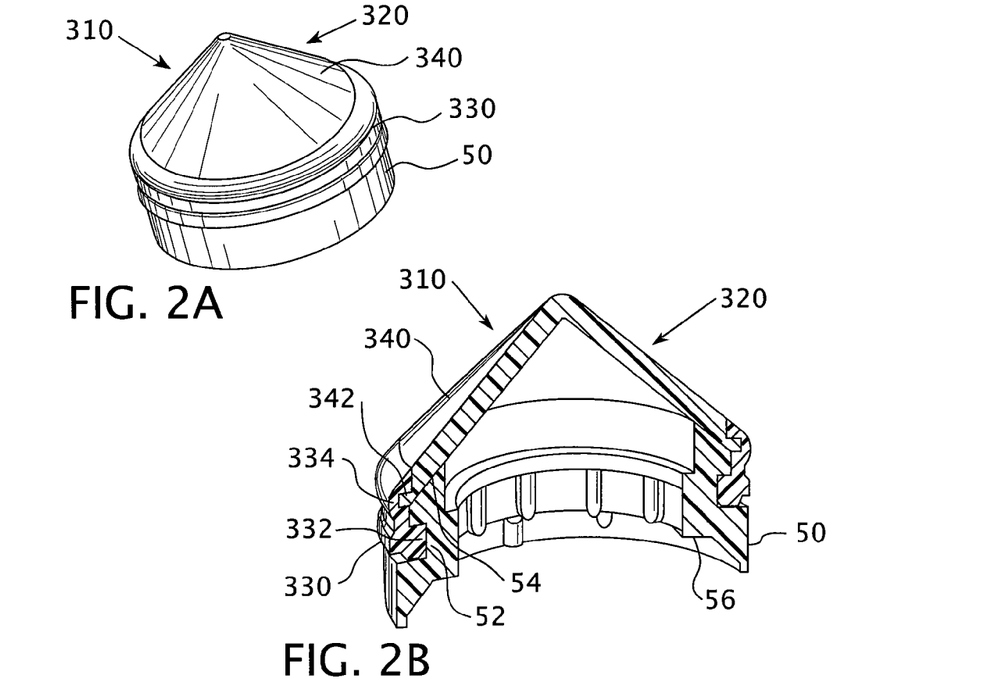
FIG. 2A illustrates a perspective view of another embodiment of a plunger of the present invention.
FIG. 2B illustrates a perspective cutaway view of the plunger of FIG. 2A.
Figure 2C:
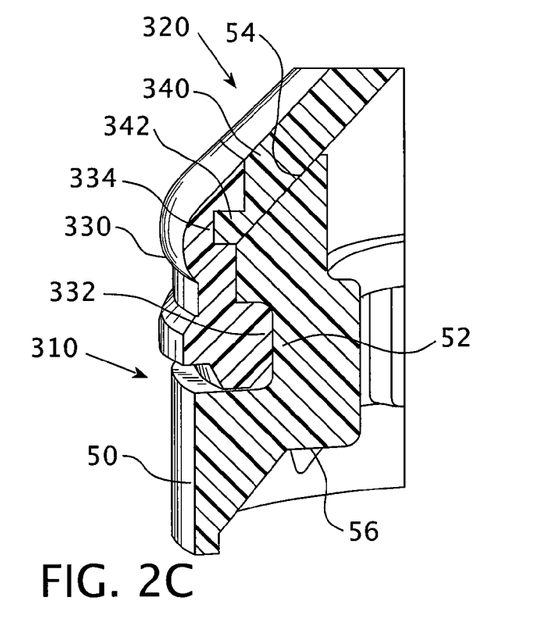
FIG. 2C illustrates an enlarged perspective cutaway view of a portion of the plunger of FIG. 2A.
Figure 2D:
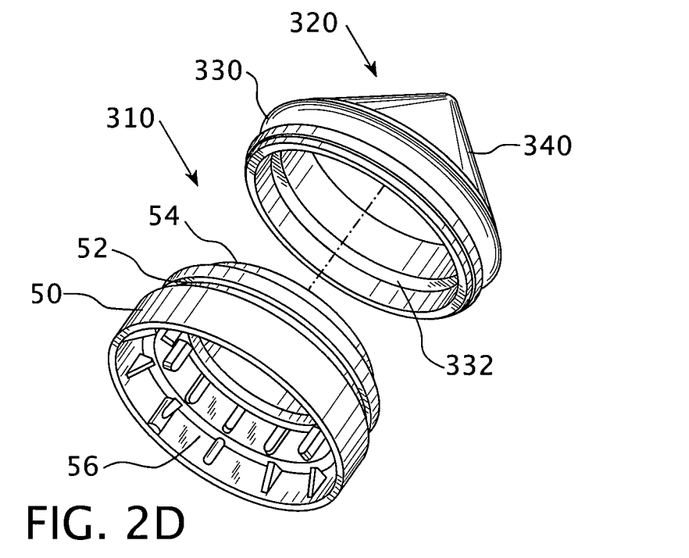
FIG. 2D illustrates a rear perspective, exploded view of the plunger of FIG. 2A wherein the plunger cover is disconnected from the base.
Figure 2E:
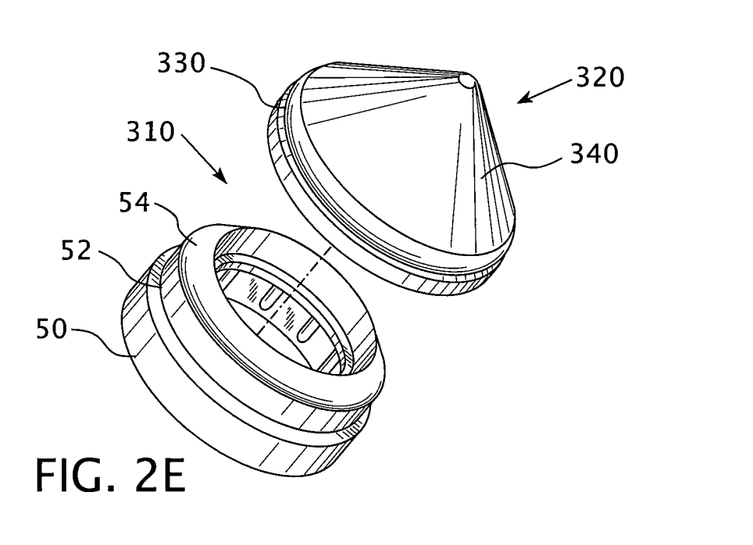
FIG. 2E illustrates a front perspective, exploded view of the plunger of FIG. 2A wherein the plunger cover is disconnected from the base.
Figures 3A, 3C:
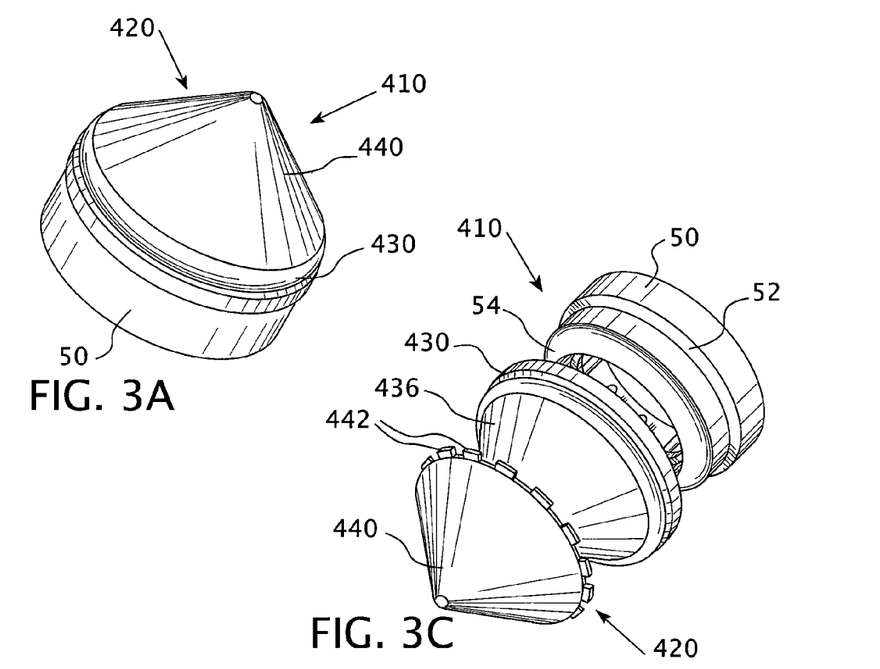
FIG. 3A illustrates a perspective view of another embodiment of a plunger of the present invention.
FIG. 3C illustrates a front perspective, exploded view of the plunger of FIG. 3A wherein the plunger cover is disconnected from the base and the sealing portion of the plunger cover is separated from the central or cone portion of the plunger cover.
Figure 3B:
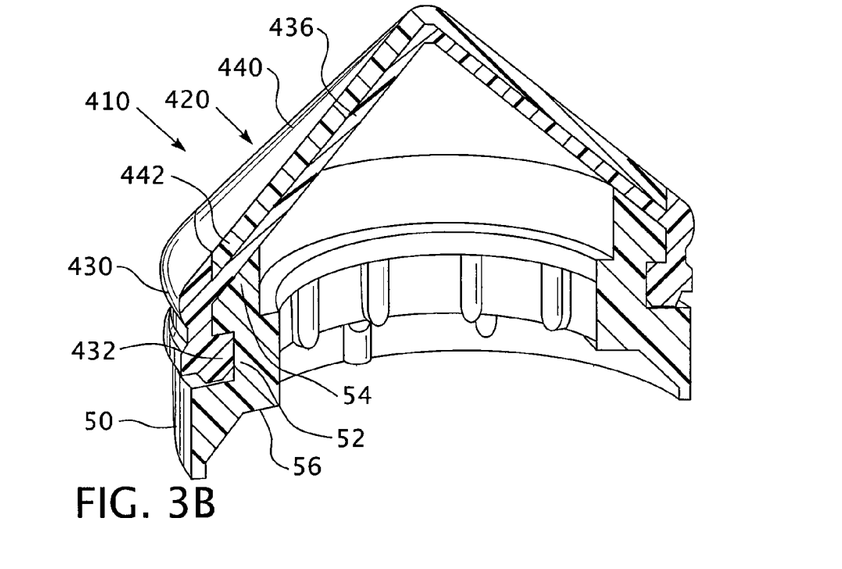
FIG. 3B illustrates a perspective cutaway view of the plunger of FIG. 3A.
Figure 3D:
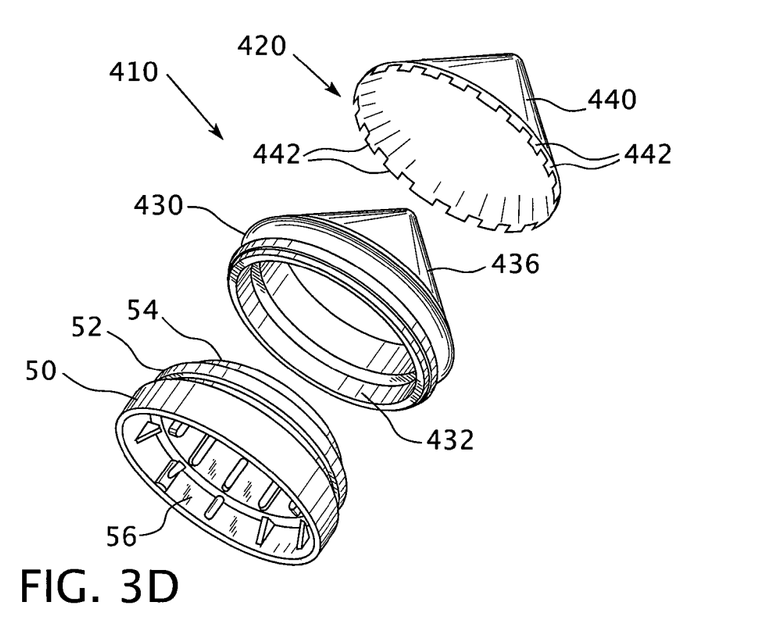
FIG. 3D illustrates a rear perspective, exploded view of the plunger of FIG. 3A wherein the plunger cover is disconnected from the base and the sealing portion of the plunger cover is separated from the central or cone portion of the plunger cover.
Figure 3E:
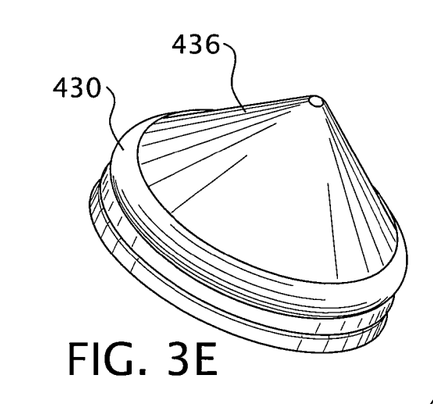
FIG. 3E illustrates a front perspective view of the sealing portion of the plunger cover of FIG. 3A.
Figure 3F:
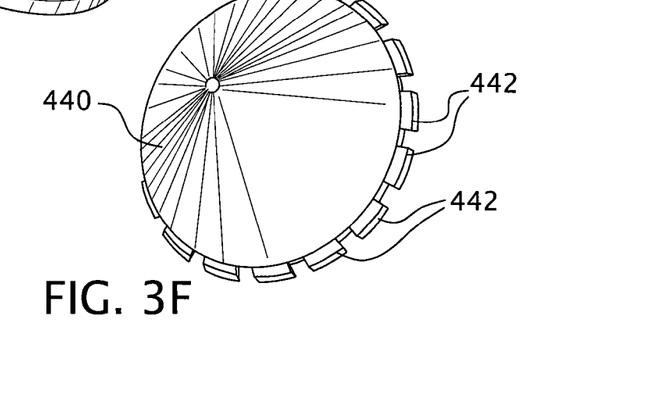
FIG. 3F illustrates a front perspective view of the central or cone portion of the plunger of FIG. 3A.
Figure 4A:
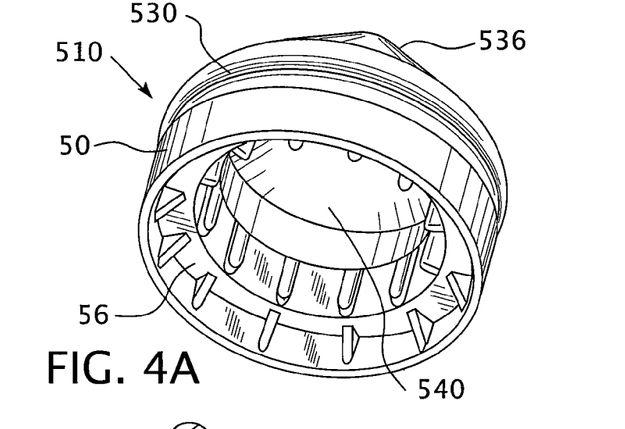
FIG. 4A illustrates a perspective view of another embodiment of a plunger of the present invention.
Figures 4B, 4C:
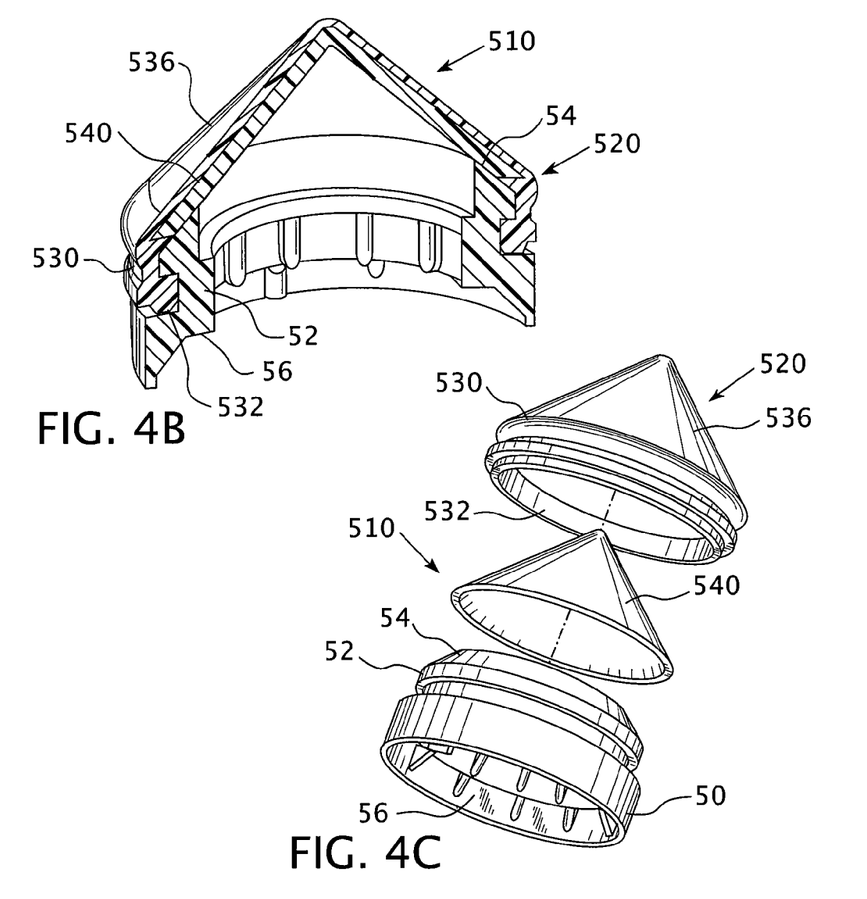
FIG. 4B illustrates a perspective cutaway view of the plunger of FIG. 3A.
FIG. 4C illustrates a front perspective, exploded view of the plunger of FIG. 4A wherein the plunger cover is disconnected from the base and the sealing portion of the plunger cover is separated from the central or cone portion of the plunger cover.
Figure 4D:
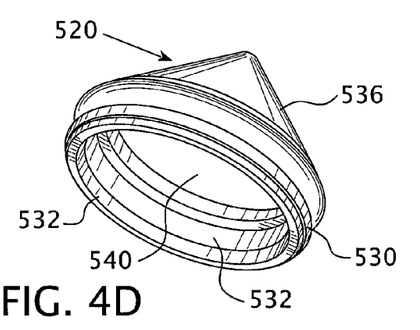
FIG. 4D illustrates a rear perspective view of the plunger cover of the plunger FIG. 4A.
Figure 4E:
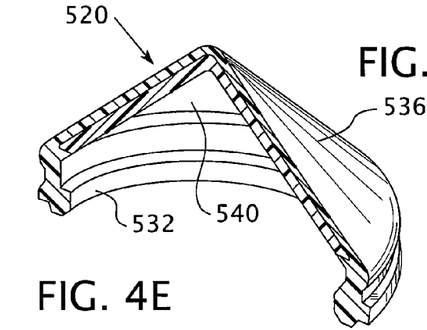
FIG. 4E illustrates a front, cutaway perspective view of the plunger cover of the plunger of FIG. 4A.
Figure 4F:
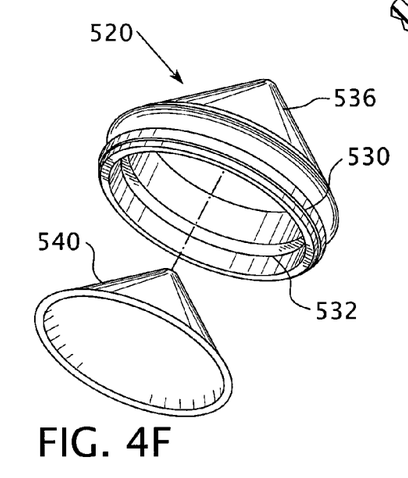
FIG. 4F illustrates a rear perspective, exploded view of the plunger cover of the plunger of FIG. 4A wherein the sealing portion of the plunger cover is separated from the central or cone portion of the plunger cover.
Figure 4G:
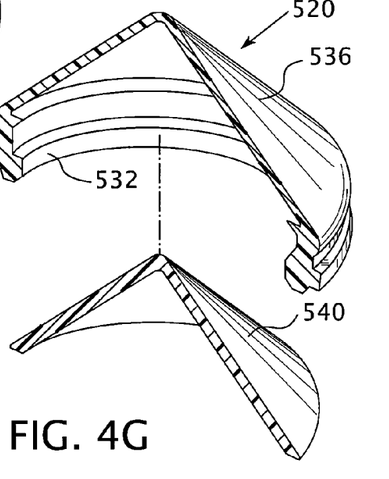
FIG. 4G illustrates a front perspective, exploded view of the plunger cover of the plunger of FIG. 4A wherein the sealing portion of the plunger cover is separated from the central or cone portion of the plunger cover.
Figure 5A:
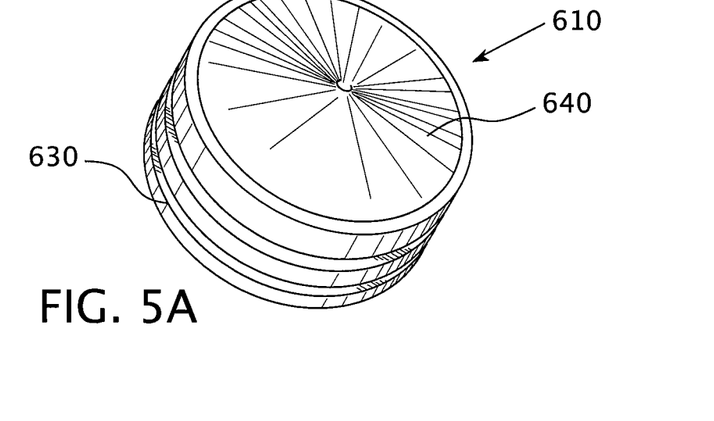
FIG. 5A illustrates a front perspective view of another embodiment of a plunger of the present invention.
Figure 5B:
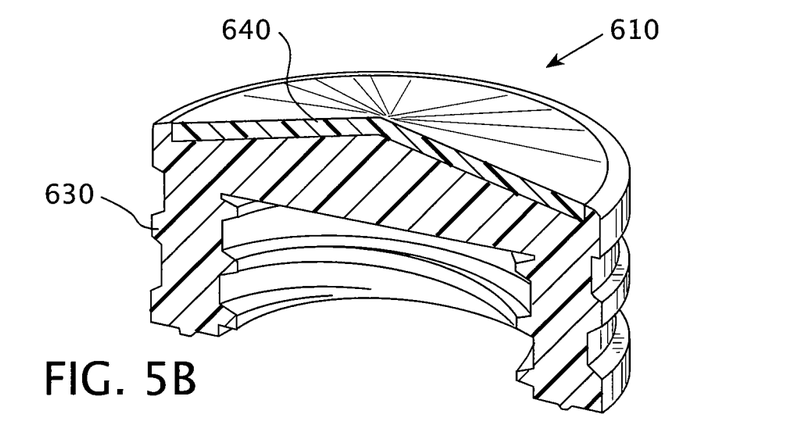
FIG. 5B illustrates a perspective, cutaway view of the plunger of FIG. 5A.
Figure 5C:
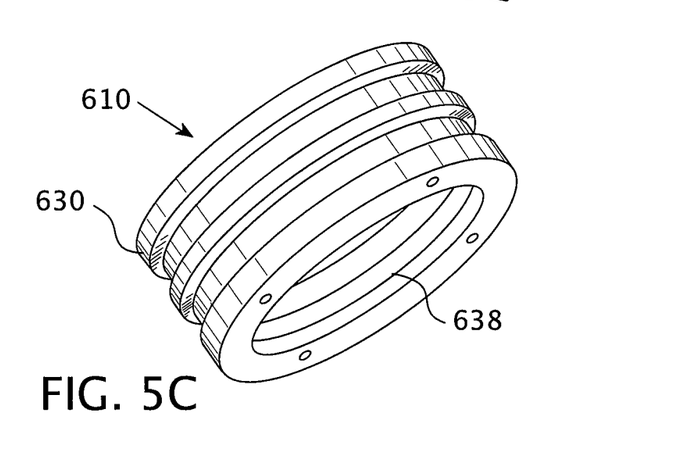
FIG. 5C illustrates a rear perspective view of the plunger of FIG. 5A.
Figure 5D:
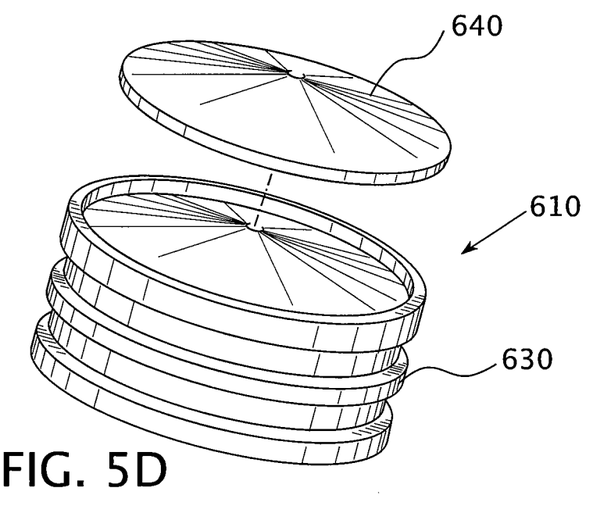
FIG. 5D illustrates a front perspective, exploded view of the plunger of FIG. 5A.
Figure 5E:
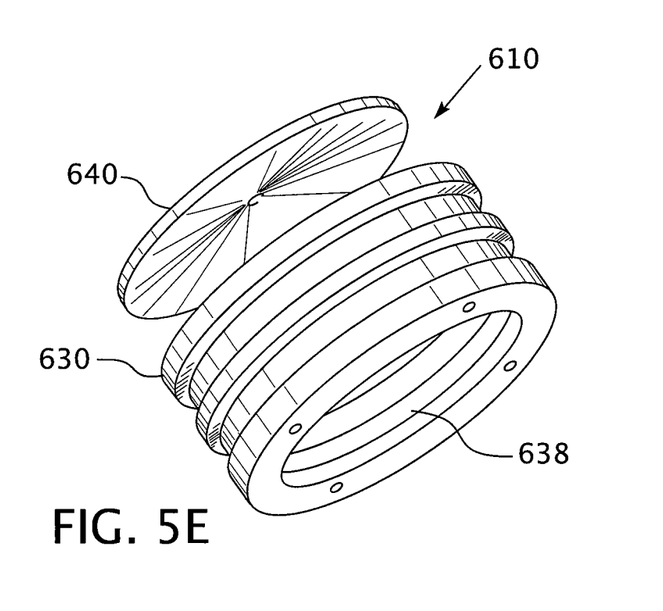
FIG. 5E illustrates a front perspective, exploded view of the plunger of FIG. 5A.

In one embodiment of an overmolding process of the present invention, sealing portion 30 of plunger cover 20 is first injection molded in an appropriately shaped mold. Examples of materials suitable for use in injection molding sealing portion 30 include thermoplastic elastomers (TPE) or thermoplastic polyurethanes (TPU). In general, a thermoplastic elastomer or thermoplastic rubber (TPR) is a polymer compound or blend which exhibits a thermoplastic character above it's melt temperature that enables it to be shaped into a fabricated article. Within the design temperature range, the material exhibits elastomeric behavior. In one embodiment, sealing portion 30 was fabricated from SANTOPRENE®, a TPE available, for example, from Advanced Elastomer Systems, L.P. of Akron, Ohio. After injection molding of sealing portion 30, central portion 40 of plunger cover 20 was molded over the TPE/TPU material of molded sealing portion 30. Central portion 40 was injection overmolded with a rigid polymeric material (for example, polypropylene, acrylonitrile butadiene styrene (ABS) or polycarbonate (PC)). Copolymers such as, for example, a PC/ABS copolymer are also suitable for use herein. The overmolding process, for example, can be done in a manual transferred operation or automatically within the same molding machine. In an insert molding process, for example, sealing portion 30 is molded first. Sealing portion 30 is then inserted into another process/mold and is overmolded over with another polymer.

The overmolded polymer does not have to be rigid polymer. The overmolded polymer can, for example, be another polymer having different physiochemical properties. A multilayered plunger/plunger cover can thereby be formed. For example, a less expensive material can be used on an inner portion of the plunger/plunger cover and a more expensive material (having better functionality—for example, a medical grade material) can be used on the outside of the plunger/plunger cover.

As known in the overmolding arts, a molecular bond can be formed between the material of sealing portion 30 and central portion 40. In addition to overmolding central portion 40 upon sealing portion 30, sealing portion 30 can be overmolded upon central portion 40. Control of the strength of the molecular bond can be achieved by appropriate selection of materials. In that regard, as known in the injection molding arts, to form a stronger molecular bond, the melt temperature of the first injected material is preferably similar to the melt temperature of the second, overmolded material. Materials that have dissimilar melt temperatures typically result in a weak molecular bond.

In addition to molecular bonding, sealing portion 30 and central portion 40 can be shaped to interconnect mechanically to add structural integrity to the connection therebetween. For example, elastomeric sealing portion 30 can be formed with a seating or groove 34 into which an extending portion 42 of central conical section 40 (see, for example, FIG. 1C) extends during the overmolding process to provide mechanical interconnection and structural integrity to the connection between sealing portion 30 and central portion 40.

As described above, elastomeric sealing portion 30 mates and form a sealing engagement with the syringe barrel wall to seal fluid inside syringe 100 As compared to plunger covers formed generally entirely of an elastomeric material via, for example, a compression molding process, central conical portion 40, formed from a relatively rigid polymeric material, provides additional structural integrity. The increased structural integrity also reduces compliance. Overmolded plunger cover 20 is a separate component of the plunger and can be assembled in various configurations (for example, with different bases or supports or without a base or support). The design and manufacturing methods associated with plunger 10 reduce manufacturing costs, while maintaining functionality. The manufacturing process provides the capability of customization of plunger cover 20. For example, colorants can be applied to the rigid polymer cone for various purposes. Moreover, the overall shape of the plunger cover can readily be altered for use with different syringes. For example, the forward portion of the plunger cover can have a conical, hemispherical, flat or other shape to mate with a correspondingly shaped syringe. In general, plunger 10 can replace currently available compression molded plunger covers in currently available plunger designs while maintaining or improving functionality of those plunger designs.

FIGS. 2A through 2E illustrate another embodiment of a plunger 310 of the present invention which is similar in design, operation and manufacture to plunger 10. In plunger 310, base or support 50 is identical to that used in plunger 10. Plunger cover 320 differs from plunger cover 20, for example, in the from of the mechanical interconnection between sealing portion 330 and central portion 340, which in the embodiment of FIGS. 2A through 2E is generally conical in shape. In that regard, For example, elastomeric sealing portion 330 is formed with a seating or groove 334 that is somewhat shorter in length than seating 34 of sealing portion 30. Similar to central portion 40, central portion 340 includes an extending portion 342 which extends into seating 334 during the overmolding process. In the embodiment of FIGS. 2A through 2E, forward surface 54 of base 50 contacts a rearward surface of central conical portion 340 directly (without any section of sealing portion 330 therebetween).

FIGS. 3A through 3F illustrate another embodiment of a plunger 410 of the present invention. Similar to plungers 10 and 310, plunger 410 includes a plunger cover 420, which includes a sealing section 430 formed, for example, from an elastomeric material such as a TPE/TPU material. Plunger cover 420 further includes a generally conical central portion 440 formed from a generally rigid polymeric material, preferably in an overmolding process. Plunger 410 further includes base or support ring 50 as described above to which plunger cover 420 is attached. In that regard, elastomeric sealing portion 430 includes a radially inward projecting flange 432 that is seatable within seating 52 formed in base 50. As with other embodiments of the present invention, however, plunger cover 420 is readily adjusted in shape and dimension to mate with a desired support.

Central portion 440 can include extending tabs 442 which can assist in forming a secure interconnection between central portion 440 and sealing portion 430. In general, such mechanical interconnections are optional in all overmolding embodiments of the present invention. In the embodiment of FIGS. 3A through 3F sealing portion 430 includes a generally conical central section 436 appropriately dimensioned such that the forward surface of central section 436 of sealing portion 430 mates with the rearward surface of rigid conical central portion 440. Central section 436 of sealing portion 430 can, for example, provide greater area for molecular bonding between central portion 440 and sealing portion 430 during the overmolding process. Central section 436 of sealing portion 430 can also provide for more effective molding of plunger cover 420 in that injection gates for sealing portion 430 and central portion 440 can have the same general location.

FIGS. 4A through 4G illustrate another embodiment of a plunger 510 of the present invention. Similar to plunger 410, plunger 510 includes a plunger cover 520, which includes a sealing portion 530 formed, for example, from an elastomeric material such as a TPE/TPU material. Plunger cover 520 further includes a generally conical central portion 540 formed from a generally rigid polymeric material, preferably in an overmolding process. Plunger 510 further includes base or support ring 50 as described above to which plunger cover 520 is attached. In that regard, elastomeric sealing portion 530 includes a radially inward projecting flange 532 that is seatable within seating 52 formed in base 50. As with other embodiments of the present invention, however, plunger cover 520 is readily adjusted in shape and dimension to mate with a desired support.

In the embodiment of FIGS. 4A through 4G central portion 540 is positioned to the rear of a generally conical central section 536 of sealing portion 430. In this embodiment, rigid central portion 540 does not contact the injection fluid, but still provides structural integrity to plunger cover 520.

FIGS. 5A through 5E illustrate another embodiment of a plunger 610 of the present invention. Unlike the plunger embodiments set forth above, plunger 610 does not include a plunger base or support as, for example, described in connection with base or support ring 50. In that regard, a sealing portion 630 (formed or molded from and elastomeric material such as a TPE/TPU material) includes a seating 638 (for example, a threaded seating) to form a connection (for example, a removable connection) with a drive member. A rigid central portion 640 can, for example, be connected with sealing portion 630 in an overmolding process as described above.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A plunger cover for use with a syringe comprising:
   a sealing portion adapted to form a seal with the syringe; and
   a central portion adapted to contact a fluid within the syringe, the central portion being more rigid than the sealing portion, the sealing portion and the central portion being connected in an overmolding process,
   wherein the sealing portion is injection molded first and the central portion is injection overmolded thereon,
   wherein the central portion comprises a conical hollow portion
   wherein the sealing portion comprises a conical central section, and
   wherein the sealing portion and the central portion are overmolded such that the conical central section and the conical hollow portion are coextensively connected to form a multilayer conical portion of the plunger cover.

2. The plunger cover of claim 1 wherein the sealing portion is formed from a thermoplastic elastomer or a thermoplastic polyurethane.

3. The plunger cover of claim 1 wherein the central portion is formed from polypropylene, acrylonitrile butadiene styrene or polycarbonate.

4. The plunger cover of claim 1 wherein a material for the sealing portion is a first material and a material for the central portion is a second material, the first material and the second material are different and are selected so that molecular bonding occurs between the sealing portion and the central portion.

5. The plunger cover of claim 1 wherein the central portion is positioned forward of at least a portion.

6. The plunger cover of claim 1 wherein the sealing portion is shaped to not contact fluid within the syringe.

7. The plunger cover of claim 1 wherein the sealing portion comprises an inwardly projecting flange seated in a seating formed in a support ring.

8. A plunger for use with a syringe comprising:
   a plunger cover comprising a sealing portion adapted to form a seal with the syringe and a central portion adapted to contact a fluid within the syringe, the central portion being more rigid than the sealing portion, the sealing portion and the central portion being connected in an overmolding process; and
   a support ring attached to the plunger cover,
   wherein the support ring has a forward surface shaped to contact and mate with a rearward surface of the plunger cover,
   wherein the central portion of the plunger cover comprises a conical hollow portion,
   wherein the sealing portion of the plunger cover comprises a conical central section, and
   wherein the sealing portion and the central portion are overmolded such that the conical central section and the conical hollow portion are coextensively connected to form a multilayer conical portion of the plunger cover.

9. The plunger of claim 8 wherein the sealing portion is formed from a thermoplastic elastomer or a thermoplastic polyurethane.

10. The plunger of claim 8 wherein the central portion is formed from polypropylene, acrylonitrile butadiene styrene or polycarbonate.

11. The plunger of claim 8 wherein a material for the sealing portion is a first material and a material for the central portion is a second material, the first material and the second material are different and are selected so that molecular bonding occurs between the sealing portion and the central portion.

12. The plunger of claim 8 wherein the material for the central portion and the material for the sealing portion are selected so that molecular bonding occurs between the central portion and the sealing portion.

13. The plunger of claim 8 wherein the sealing portion includes a radially inward projecting flange that is seated within a seating formed on the support ring to connect the plunger cover to the support ring.

14. The plunger of claim 8 wherein the forward surface of the support ring abuts the plunger cover to prevent rearward motion of the central portion of the plunger cover relative to the support ring.

15. A syringe comprising:
   a syringe body and a plunger slidably positioned within the syringe body, the plunger comprising a plunger cover comprising:
      a sealing portion adapted to form a seal with the syringe body;
      a central portion adapted to contact a fluid within the syringe, the central portion being more rigid than the sealing portion, the sealing portion and the central portion being connected in an overmolding process; and
      a support ring attached to the plunger cover,
   wherein the sealing portion is injection molded first and the central portion is injection molded thereon,
   wherein the support ring has a forward surface shaped to contact and mate with a rearward surface of the plunger cover,
   wherein the central portion comprises a conical hollow portion,
   wherein the sealing portion comprises a conical central section, and
   wherein the sealing portion and the central portion are overmolded such that the conical central section and the conical hollow portion are coextensively connected to form a multilayer conical portion of the plunger cover.

16. A method of fabricating a plunger cover for use in a syringe, the method comprising:
   molding a sealing portion adapted to form a seal with the syringe;
   molding a central portion adapted to contact a fluid within the syringe; and
   connecting the sealing portion and the central portion in an overmolding process, the central portion being more rigid than the sealing portion,
   wherein the central portion comprises a conical hollow portion, and
   wherein the sealing portion comprises a conical central section, and
   wherein the sealing portion and the central portion are overmolded such that the conical central section and the conical hollow portion are coextensively connected to form a multilayer conical portion of the plunger cover.

17. The method of claim 16 wherein the sealing portion is injection molded first and the central portion is injection overmolded thereon.

18. A plunger cover for use with a syringe comprising:
   a sealing portion adapted to form a seal with the syringe and a central portion adapted to contact fluid within the syringe, the central portion having at least one physiochemical property that differs from the sealing portion, the sealing portion and the central portion being connected in an overmolding process,
   wherein the central portion is overmolded upon the sealing portion,
   wherein the central portion comprises a conical hollow portion,
   wherein the sealing portion comprises a conical central section, and
   wherein the sealing portion and central portion are overmolded such that the conical central section and the conical hollow portion are coextensively connected to form a multilayer conical portion of the plunger cover.

* * * * *